(12) United States Patent
Shanley et al.

(10) Patent No.: US 7,169,179 B2
(45) Date of Patent: Jan. 30, 2007

(54) DRUG DELIVERY DEVICE AND METHOD FOR BI-DIRECTIONAL DRUG DELIVERY

(75) Inventors: John F. Shanley, Redwood City, CA (US); Theodore L. Parker, Danville, CA (US)

(73) Assignee: Conor Medsystems, Inc., Menlo Park, CA (US)

( * ) Notice: Subject to any disclaimer, the term of this patent is extended or adjusted under 35 U.S.C. 154(b) by 418 days.

(21) Appl. No.: 10/456,432

(22) Filed: Jun. 5, 2003

(65) Prior Publication Data

US 2004/0249449 A1     Dec. 9, 2004

(51) Int. Cl.
    *A61F 2/06* (2006.01)
(52) U.S. Cl. ..................... 623/1.43; 623/1.42
(58) Field of Classification Search ............... 623/1.42, 623/1.43
    See application file for complete search history.

(56) References Cited

U.S. PATENT DOCUMENTS

| | | | |
|---|---|---|---|
| 3,657,744 A | 4/1972 | Ersek |
| 4,542,025 A | 9/1985 | Tice et al. |
| 4,580,568 A | 4/1986 | Gianturco |
| 4,650,466 A | 3/1987 | Luther |
| 4,733,665 A | 3/1988 | Palmaz |
| 4,739,762 A | 4/1988 | Palmaz |
| 4,776,337 A | 10/1988 | Palmaz |
| 4,800,882 A | 1/1989 | Gianturco |
| 4,824,436 A | 4/1989 | Wolinsky |
| 4,834,755 A | 5/1989 | Silverstrini et al. |
| 4,955,878 A | 9/1990 | See et al. |
| 4,957,508 A | 9/1990 | Kaneko et al. |
| 4,960,790 A | 10/1990 | Stella et al. |
| 4,969,458 A | 11/1990 | Wiktor |
| 4,989,601 A | 2/1991 | Marchosky et al. |
| 4,990,155 A | 2/1991 | Wilkoff |
| 4,994,071 A | 2/1991 | MacGregor |

(Continued)

FOREIGN PATENT DOCUMENTS

CA         2234787         10/1998

(Continued)

OTHER PUBLICATIONS

Jennifer L. West, "Drug Delivery—Pulsed Polymers". Nature Materials, vol. 2, Nov. 2003, pp. 709-710.

Hwang, C-W. Et al., "*Physiological Transport Forces Govern Drug Distribution for Stent Based Delivery*", Circulation, (Aug. 17, 2001), pp. 1-8.

*Primary Examiner*—Eduardo C. Robert
*Assistant Examiner*—Thomas J. Sweet
(74) *Attorney, Agent, or Firm*—Cindy A. Lynch (57) ABSTRACT

A drug delivery device is provided with openings for directional delivery of a plurality of therapeutic agents to blood vessels or other lumens or organs. In particular, the invention relates to the delivery of different therapeutic agents, different quantities of therapeutic agents, or different release profiles of the same or different therapeutic agents in different directions from the drug delivery device. The invention is useful, for example, for delivering antirestenotic, antithrombotic, antiplatelet, antiproliferative, antineoplastic, immunosuppressive, angiogenic, anti-inflammatory, or anti-angiogenic agents and/or vasodilators to a blood vessel. In one embodiment, antiproliferative, antineoplastic, angiogenic, antiangiogenic, anti-inflammatory, and/or antirestenotic agents are delivered to the wall of a blood vessel and antithrombotic agents, antiplatelet agents, and/or vasodilators are delivered to the lumen of a blood vessel.

20 Claims, 1 Drawing Sheet

U.S. PATENT DOCUMENTS

| | | |
|---|---|---|
| 5,019,090 A | 5/1991 | Pinchuk |
| 5,049,132 A | 9/1991 | Shaffer et al. |
| 5,053,048 A | 10/1991 | Pinchuk |
| 5,059,166 A | 10/1991 | Fischell et al. |
| 5,059,211 A | 10/1991 | Stack et al. |
| 5,078,726 A | 1/1992 | Kreamer |
| 5,092,841 A | 3/1992 | Spears |
| 5,102,417 A | 4/1992 | Palmaz |
| 5,157,049 A | 10/1992 | Haugwitz et al. |
| 5,171,217 A | 12/1992 | March et al. |
| 5,171,262 A | 12/1992 | MacGregor |
| 5,176,617 A | 1/1993 | Fischell et al. |
| 5,195,984 A | 3/1993 | Schatz |
| 5,197,978 A | 3/1993 | Hess |
| 5,213,580 A | 5/1993 | Slepian et al. |
| 5,234,456 A | 8/1993 | Silvestrini |
| 5,242,399 A | 9/1993 | Lau et al. |
| 5,286,254 A | 2/1994 | Shapland et al. |
| 5,292,512 A | 3/1994 | Schaefer et al. |
| 5,304,121 A | 4/1994 | Sahatjian |
| 5,314,688 A | 5/1994 | Kauffamn et al. |
| 5,342,348 A | 8/1994 | Kaplan |
| 5,342,621 A | 8/1994 | Eury |
| 5,344,426 A | 9/1994 | Lau et al. |
| 5,380,299 A | 1/1995 | Fearnot et al. |
| 5,383,892 A | 1/1995 | Cardon et al. |
| 5,383,928 A | 1/1995 | Scott et al. |
| 5,403,858 A | 4/1995 | Bastard et al. |
| 5,407,683 A | 4/1995 | Shively |
| 5,415,869 A | 5/1995 | Straubinger et al. |
| 5,419,760 A | 5/1995 | Narciso, Jr. |
| 5,439,446 A | 8/1995 | Barry |
| 5,439,686 A | 8/1995 | Desai et al. |
| 5,441,515 A | 8/1995 | Khosravi et al. |
| 5,441,745 A | 8/1995 | Presant et al. |
| 5,443,496 A | 8/1995 | Schwartz et al. |
| 5,443,497 A | 8/1995 | Venbrux |
| 5,443,500 A | 8/1995 | Sigwart |
| 5,447,724 A | 9/1995 | Helmus et al. |
| 5,449,373 A | 9/1995 | Pinchasik et al. |
| 5,449,513 A | 9/1995 | Yokoyama et al. |
| 5,457,113 A | 10/1995 | Cullinan et al. |
| 5,460,817 A | 10/1995 | Langley et al. |
| 5,462,866 A | 10/1995 | Wang |
| 5,464,450 A | 11/1995 | Buscemi et al. |
| 5,464,650 A | 11/1995 | Berg et al. |
| 5,473,055 A | 12/1995 | Mongelli et al. |
| 5,523,092 A | 6/1996 | Hanson et al. |
| 5,545,210 A | 8/1996 | Hess et al. |
| 5,551,954 A | 9/1996 | Buscemi et al. |
| 5,556,413 A | 9/1996 | Lam |
| 5,575,771 A | 11/1996 | Walinsky |
| 5,578,075 A | 11/1996 | Dayton |
| 5,593,434 A | 1/1997 | Williams |
| 5,607,442 A | 3/1997 | Fischell et al. |
| 5,609,629 A | 3/1997 | Fearnot et al. |
| 5,616,608 A | 4/1997 | Kinsella et al. |
| 5,617,878 A | 4/1997 | Taheri |
| 5,618,299 A | 4/1997 | Khosravi et al. |
| 5,624,411 A | 4/1997 | Tuch |
| 5,628,787 A | 5/1997 | Mayer |
| 5,643,314 A | 7/1997 | Carpenter et al. |
| 5,667,764 A | 9/1997 | Kopia et al. |
| 5,674,278 A | 10/1997 | Boneau |
| 5,697,971 A | 12/1997 | Fischell et al. |
| 5,707,385 A | 1/1998 | Williams |
| 5,713,949 A | 2/1998 | Jayaraman |
| 5,716,981 A | 2/1998 | Hunter et al. |
| 5,725,548 A | 3/1998 | Jayaraman |
| 5,725,549 A | 3/1998 | Lam |
| 5,733,330 A | 3/1998 | Cox |
| 5,733,925 A | 3/1998 | Kunz et al. |
| 5,741,293 A | 4/1998 | Wijay |
| 5,759,192 A | 6/1998 | Saunders |
| 5,766,239 A | 6/1998 | Cox |
| 5,769,883 A | 6/1998 | Buscemi et al. |
| 5,776,181 A | 7/1998 | Lee et al. |
| 5,797,898 A | 8/1998 | Santini et al. |
| 5,800,507 A | 9/1998 | Schwartz |
| 5,807,404 A | 9/1998 | Richter |
| 5,817,152 A | 10/1998 | Birdsall et al. |
| 5,824,045 A | 10/1998 | Alt |
| 5,824,049 A | 10/1998 | Ragheb et al. |
| 5,827,322 A | 10/1998 | Williams |
| 5,837,313 A | 11/1998 | Ding et al. |
| 5,843,117 A | 12/1998 | Alt et al. |
| 5,843,120 A | 12/1998 | Israel et al. |
| 5,843,172 A | 12/1998 | Yan |
| 5,843,175 A | 12/1998 | Frantzen |
| 5,843,741 A | 12/1998 | Wong et al. |
| 5,853,419 A | 12/1998 | Imran |
| 5,855,600 A | 1/1999 | Alt |
| 5,868,781 A | 2/1999 | Killion |
| 5,873,904 A | 2/1999 | Ragheb et al. |
| 5,876,419 A | 3/1999 | Carpenter et al. |
| 5,882,335 A | 3/1999 | Leone et al. |
| 5,886,026 A | 3/1999 | Hunter et al. |
| 5,922,020 A | 7/1999 | Klein et al. |
| 5,922,021 A | 7/1999 | Jang |
| 5,957,971 A | 9/1999 | Schwartz |
| 5,964,798 A | 10/1999 | Imran |
| 5,968,092 A | 10/1999 | Buscemi et al. |
| 5,972,027 A | 10/1999 | Johnson |
| 5,976,182 A | 11/1999 | Cox |
| 5,984,957 A | 11/1999 | Laptewicz, Jr. et al. |
| 5,992,769 A | 11/1999 | Wise |
| 6,007,517 A | 12/1999 | Anderson |
| 6,017,363 A | 1/2000 | Hojeibane |
| 6,019,789 A | 2/2000 | Dinh et al. |
| 6,022,371 A | 2/2000 | Killion |
| 6,030,414 A | 2/2000 | Taheri |
| 6,042,606 A | 3/2000 | Frantzer |
| 6,056,722 A | 5/2000 | Jayaraman |
| 6,063,101 A | 5/2000 | Jacobsen et al. |
| 6,071,305 A | 6/2000 | Brown et al. |
| 6,083,258 A | 7/2000 | Yadav |
| 6,087,479 A | 7/2000 | Stamler et al. |
| 6,096,070 A | 8/2000 | Ragheb et al. |
| 6,099,561 A | 8/2000 | Alt |
| 6,120,535 A | 9/2000 | McDonald et al. |
| 6,120,847 A | 9/2000 | Yang et al. |
| 6,123,861 A | 9/2000 | Santini et al. |
| 6,153,252 A | 11/2000 | Hossainy et al. |
| 6,156,062 A | 12/2000 | McGuinness |
| 6,159,488 A | 12/2000 | Nagler et al. |
| 6,174,326 B1 | 1/2001 | Kitaoka et al. |
| 6,193,746 B1 | 2/2001 | Strecker |
| 6,206,914 B1 | 3/2001 | Soykan et al. |
| 6,206,915 B1 | 3/2001 | Fagan et al. |
| 6,206,916 B1 | 3/2001 | Furst |
| 6,231,600 B1 | 5/2001 | Zhong |
| 6,240,616 B1 | 6/2001 | Yan |
| 6,241,762 B1 | 6/2001 | Shanley |
| 6,245,101 B1 | 6/2001 | Drasler et al. |
| 6,249,952 B1 | 6/2001 | Ding |
| 6,254,632 B1 | 7/2001 | Wu et al. |
| 6,273,908 B1 | 8/2001 | Ndondo-Lay |
| 6,273,910 B1 | 8/2001 | Limon |
| 6,273,913 B1 | 8/2001 | Wright et al. |
| 6,280,411 B1 | 8/2001 | Lennox |
| 6,290,673 B1 | 9/2001 | Shanley |
| 6,293,967 B1 | 9/2001 | Shanley |
| 6,299,604 B1 | 10/2001 | Ragheb et al. |
| 6,309,414 B1 | 10/2001 | Rolando et al. |

| | | | | | | |
|---|---|---|---|---|---|---|
| 6,312,460 B2 | 11/2001 | Drasler et al. | EP | 0 679 373 | 11/1995 |
| 6,379,381 B1 | 4/2002 | Hossainy et al. | EP | 0 706 376 | 4/1996 |
| 6,395,326 B1 | 5/2002 | Castro et al. | EP | 0 734 698 | 10/1996 |
| 6,423,092 B2 | 7/2002 | Datta et al. | EP | 0 747 069 | 12/1996 |
| 6,451,051 B2 | 9/2002 | Drasler et al. | EP | 0747069 | 12/1996 |
| 6,475,237 B2 | 11/2002 | Drasler et al. | EP | 0 770 401 | 5/1997 |
| 6,491,666 B1 | 12/2002 | Santini et al. | EP | 0 897 700 | 2/1999 |
| 6,506,411 B2 | 1/2003 | Hunter et al. | EP | 0 950 386 | 10/1999 |
| 6,506,437 B1 | 1/2003 | Harish et al. | EP | 1 118 325 | 7/2001 |
| 6,537,256 B2 | 3/2003 | Santini et al. | EP | 1 132 058 | 9/2001 |
| 6,544,544 B2 | 4/2003 | Hunter et al. | EP | 1 172 074 | 1/2002 |
| 6,551,838 B2 | 4/2003 | Santini et al. | EP | 1172074 | 1/2002 |
| 6,558,733 B1 | 5/2003 | Hossainy | EP | 1 223 305 | 7/2002 |
| 6,562,065 B1 | 5/2003 | Shanley | EP | 1222941 | 7/2002 |
| 6,585,764 B2 | 7/2003 | Wright et al. | EP | 1 236 478 | 9/2002 |
| 6,656,162 B2 | 12/2003 | Santini et al. | FR | 2 764 794 | 12/1998 |
| 6,660,034 B1 | 12/2003 | Mandrusov et al. | WO | WO 90/13332 | 11/1990 |
| 6,730,064 B2 | 5/2004 | Ragheb et al. | WO | WO 91/10424 | 7/1991 |
| 6,730,116 B1 | 5/2004 | Wolinsky et al. | WO | WO 91/11193 | 8/1991 |
| 6,758,859 B1 | 7/2004 | Dang et al. | WO | WO 91/12779 | 9/1991 |
| 2001/0000802 A1 | 5/2001 | Soykan et al. | WO | WO 92/12717 | 8/1992 |
| 2001/0027340 A1 | 10/2001 | Wright et al. | WO | WO 92/15286 | 9/1992 |
| 2001/0029351 A1 | 10/2001 | Falotico et al. | WO | WO 93/06792 | 4/1993 |
| 2001/0034363 A1 | 10/2001 | Li et al. | WO | WO 94/21308 | 9/1994 |
| 2001/0044648 A1 | 11/2001 | Wolinsky et al. | WO | WO 94/24961 | 11/1994 |
| 2001/0044652 A1 | 11/2001 | Moore | WO | WO 95/03036 | 2/1995 |
| 2002/0002400 A1 | 1/2002 | Drasler et al. | WO | WO 95/03795 | 2/1995 |
| 2002/0005206 A1 | 1/2002 | Falotico et al. | WO | WO 95/24908 | 9/1995 |
| 2002/0007209 A1 | 1/2002 | De Scheerder et al. | WO | WO 96/03092 | 2/1996 |
| 2002/0022876 A1 | 2/2002 | Richter et al. | WO | WO 96/25176 | 8/1996 |
| 2002/0032414 A1 | 3/2002 | Ragheb et al. | WO | WO 96/29028 | 9/1996 |
| 2002/0038145 A1 | 3/2002 | Jang | WO | WO 96/32907 | 10/1996 |
| 2002/0068969 A1 | 6/2002 | Shanley et al. | WO | WO 97/04721 | 2/1997 |
| 2002/0072511 A1 | 6/2002 | New et al. | WO | WO 98/08566 | 3/1998 |
| 2002/0082679 A1 | 6/2002 | Sirhan et al. | WO | WO 98/18407 | 5/1998 |
| 2002/0082680 A1 | 6/2002 | Shanley et al. | WO | WO 98/19628 | 5/1998 |
| 2002/0094985 A1 | 7/2002 | Herrmann et al. | WO | WO 98/23228 | 6/1998 |
| 2002/0123801 A1 | 9/2002 | Pacetti et al. | WO | WO 98/23244 | 6/1998 |
| 2002/0142039 A1 | 10/2002 | Claude | WO | WO 98/36784 | 8/1998 |
| 2002/0155212 A1 | 10/2002 | Hossainy | WO | WO-9836784 | 8/1998 |
| 2003/0028243 A1 | 2/2003 | Bates et al. | WO | WO 98/58600 | 12/1998 |
| 2003/0028244 A1 | 2/2003 | Bates et al. | WO | WO 99/15108 | 4/1999 |
| 2003/0036794 A1 | 2/2003 | Ragheb et al. | WO | WO 99/16386 | 4/1999 |
| 2003/0060877 A1 | 3/2003 | Falotico et al. | WO | WO 99/16477 | 4/1999 |
| 2003/0068355 A1 | 4/2003 | Shanley et al. | WO | WO-9916386 | 4/1999 |
| 2003/0100865 A1 | 5/2003 | Santini et al. | WO | WO 99/44536 | 9/1999 |
| 2003/0125803 A1 | 7/2003 | Vallana et al. | WO | WO 99/49928 | 10/1999 |
| 2003/0176915 A1 | 9/2003 | Wright et al. | WO | WO-9949928 | 10/1999 |
| 2003/0199970 A1 | 10/2003 | Shanley | WO | WO 99/55396 | 11/1999 |
| 2003/0216699 A1 | 11/2003 | Falotico | WO | WO 00/10613 | 3/2000 |
| 2004/0122505 A1 | 6/2004 | Shanley | WO | WO-0010622 | 3/2000 |
| 2004/0122506 A1 | 6/2004 | Shanley et al. | WO | WO 00/45744 | 8/2000 |
| 2004/0127976 A1 | 7/2004 | Diaz | WO | WO 00/69368 | 11/2000 |
| 2004/0127977 A1 | 7/2004 | Shanley | WO | WO 00/71054 | 11/2000 |
| | | | WO | WO 01/17577 | 3/2001 |

FOREIGN PATENT DOCUMENTS

| | | | | | |
|---|---|---|---|---|---|
| | | | WO | WO-0117577 | 3/2001 |
| DE | 202 00 220 | 3/2002 | WO | WO 01/45862 | 6/2001 |
| EP | 0 335 341 | 10/1989 | WO | WO 01/49338 | 7/2001 |
| EP | 0 375 520 | 6/1990 | WO | WO 01/87376 | 11/2001 |
| EP | 0 470 246 | 2/1992 | WO | WO 02/17880 | 3/2002 |
| EP | 0 470 569 | 2/1992 | WO | WO 02/26281 | 4/2002 |
| EP | 0 566 245 | 10/1993 | WO | WO-0226281 | 4/2002 |
| EP | 0 567 816 | 11/1993 | WO | WO-04043510 | 5/2004 |
| EP | 0 627 226 | 12/1994 | WO | WO-04043511 | 5/2004 |

DRUG DELIVERY DEVICE AND METHOD FOR BI-DIRECTIONAL DRUG DELIVERY

BACKGROUND OF THE INVENTION

Field of the Invention

The invention relates to the use of a drug delivery device with openings to deliver a plurality of beneficial agents to bodily lumens. In particular, the invention relates to the delivery of different beneficial agents, different quantities of beneficial agents, or different release profiles of the same or different beneficial agents in different directions from the drug delivery device.

REFERENCES

Allison, A. C. (2000) Immunosuppressive drugs: the first 50 years and a glance forward. Immunopharmacology. 47:63–83;
Dogne, J. M. et al. (2002) Recent advances in antiplatelet agents. Curr. Med. Chem. 9:577–89;
Kirsten, R. et al. (1998) Clinical pharmacokinetics of vasodilators. Part I. Clin. Pharmacokinet. 34:457–82;
Kirsten, R. et al. (1998) Clinical pharmacokinetics of vasodilators. Part II. Clin. Pharmacokinet. 35:9–36;
Kitakaze, M. et al. (2002) Angiotensin-converting enzyme inhibitors and angiotensin II receptor blockers synergistically increase coronary blood flow in canine ischemic myocardium: role of bradykinin. J. Am. Coll. Cardiol. 40:162–6;
Oikawa, Y. et al. (2001) Attenuation of angiotensin II-mediated coronary vasoconstriction and vasodilatory action of angiotensin-converting enzyme inhibitor in pacing-induced heart failure in dogs. J. Am. Coll. Cardiol. 38:1188–94;
Physicians' Desk Reference (2001) Medical Economics Co., Inc., Montvale, N. J.;
Sun, Y. P. et al. (2001) Comparative effects of ACE inhibitors and an angiotensin receptor blocker on atherosclerosis and vascular function. J. Cardiovasc. Pharmacol. Ther. 6:175–81;
Tanoue, A. et al. (2001) The alpha(1D)-adrenergic receptor directly regulates arterial blood pressure via vasoconstriction. J. Clin. Invest. 109:765–75;
U.S. Pat. No. 4,446,325;
U.S. Pat. No. 4,733,665;
U.S. Pat. No. 4,733,665;
U.S. Pat. No. 4,733,665;
U.S. Pat. No. 4,739,762;
U.S. Pat. No. 4,739,762;
U.S. Pat. No. 4,776,337;
U.S. Pat. No. 4,776,337;
U.S. Pat. No. 4,776,337;
U.S. Pat. No. 4,969,458;
U.S. Pat. No. 5,116,861;
U.S. Pat. No. 5,284,834;
U.S. Pat. No. 5,716,981;
U.S. Pat. No. 5,972,965;
U.S. Pat. No. 6,241,762;
U.S. Pat. No. 6,440,948;
U.S. Pat. No. 6,476,037;
U.S. Pat. No. 6,489,298;
Van Aken, H. et al. (2001) Anticoagulation: the present and future. Clin. Appl. Thromb. Hemost. 7:195–204;

SUMMARY OF THE RELATED ART

Permanent and biodegradable devices have been developed for implantation within a body passageway to maintain patency of the passageway. These devices have typically been introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and thin-walled metal cylinders with axial slots formed around the circumference (U.S. Pat. Nos. 4,733,665; 4,739,762; and 4,776,337). Known construction materials for use in stents include polymers, organic fabrics, and biocompatible metals, such as, stainless steel, gold, silver, tantalum, titanium, and shape memory alloys such as Nitinol.

U.S. Pat. Nos. 4,733,665; 4,739,762; and 4,776,337 disclose expandable and deformable interluminal vascular grafts in the form of thin-walled tubular members with axial slots allowing the members to be expanded radially outwardly into contact with a body passageway. After insertion, the tubular members are mechanically expanded beyond their elastic limit and thus permanently fixed within the body.

Coated stents, designed to release various beneficial agents, have shown promising results in reducing restenosis, a condition commonly associated with stent implantation. For example, U.S. Pat. No. 5,716,981 discloses a stent that is surface-coated with an agent comprising a polymer carrier and Paclitaxel, a well-known tubulin assembly stabilizer that is commonly used in the treatment of cancerous tumors.

In addition, several U.S. patents describe the use of stents to deliver angiogenic agents (U.S. Pat. Nos. 6,479,654; 6,475,779; and 6,363,938), antithrombotic (antiplatelet) agents (U.S. Pat. Nos. 6,071,514 and 5,383,928), anticoagulants (U.S. Pat. No. 6,273,908), or combinations thereof (U.S. Pat. No. 6,231,600).

However, a major technological obstacle facing the use of stents for the delivery of angiogenic agents is the thickness of the stent coating. Stent coatings are necessarily very thin, typically 5 to 8 microns. Since the surface area of the stent is comparatively large, the entire volume of the beneficial agent has a very short diffusion path to discharge into the surrounding tissue. This issue is especially problematic for therapies that require the prolonged delivery of a beneficial agent. While increasing the thickness of the surface coating improves drug release kinetics, it also results in an undesirable increase in overall stent thickness.

Moreover, existing methods of drug delivery using coated stents are unable to selectively deliver beneficial agents to only one side of the stent surface and are unable to deliver different beneficial agents to different surfaces of the implanted stent, for example, the exterior surface adjacent to the wall of the blood vessel and the interior surface exposed to the lumen of the blood vessel.

The instant invention satisfies a need in the art by providing a medical device that can provide different beneficial agents, different quantities of beneficial agents, or different release profiles of the same or different beneficial agents in different directions with respect to the surfaces of the medical device.

SUMMARY OF THE INVENTION

In accordance with one embodiment of the invention, a drug delivery device includes first and second therapeutic agents arranged for delivery in different directions.

In one embodiment, a method of delivering therapeutic agents comprises the steps of providing a medical device comprising an exterior surface and an interior surface, and first and second therapeutic agents in openings in the medical device, implanting the medical device with the therapeutic agents in a patient, releasing the first therapeutic agent predominantly in a direction of said exterior surface of the medical device over a time period sufficient to produce a therapeutic effect, and releasing the second therapeutic agent predominantly in a direction of said interior surface of the medical device over a time period sufficient to produce a therapeutic effect.

In another embodiment, a method of delivering two or more therapeutic agents, to a blood vessel includes providing a substantially cylindrical medical device having an exterior surface, an interior surface, and openings traversing said exterior surface and said interior surface, said openings having a barrier layer arranged at a radially intermediate surface with respect to said exterior surface and said interior surface, wherein at least one first therapeutic agent is disposed in a therapeutic layer disposed at a radially exterior surface with respect to said barrier layer and wherein at least one second therapeutic agent is disposed in a therapeutic layer disposed at a radially interior surface with respect to said barrier layer, delivering the medical device with the therapeutic agents to a lumen of a blood vessel, and releasing the therapeutic agents over a time period sufficient to produce a therapeutic effect, wherein the first therapeutic agent is released substantially toward said exterior surface of the medical device and wherein the second therapeutic agent is released substantially toward said interior surface of the medical device.

In a further embodiment, a method of delivering therapeutic agents to a blood vessel comprises providing a medical device comprising a first surface, a second surface, and openings traversing said first surface and said second surface, said openings containing therapeutic agents, delivering the medical device with the therapeutic agents to a lumen of a blood vessel, and releasing a first of the therapeutic agents to a wall of the blood vessel over a time period sufficient to produce a therapeutic effect, and releasing a second of the therapeutic agents to the lumen of the blood vessel over a time period sufficient to produce a therapeutic effect.

In another embodiment, a drug delivery device comprises a medical device having an exterior surface and an interior surface, a plurality of openings in the device body, and a first therapeutic agent and a second therapeutic agent disposed in the openings and arranged to deliver the first therapeutic agent primarily to the exterior surface and to deliver the second therapeutic agent primarily to the interior surface.

In a further embodiment, a drug delivery device comprises an exterior surface, an interior surface, a plurality of openings traversing said exterior surface and said interior surface, said openings having a barrier layer arranged at a radially intermediate position with respect to said exterior surface and said interior surface, at least one first therapeutic agent in a therapeutic layer disposed at a radially exterior position with respect to said barrier layer, and at least one second therapeutic agent in a therapeutic layer disposed at a radially interior position with respect to said barrier layer.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

Definitions

As used herein, the following terms have the following meanings:

Angiogenesis: The process by which a capillary network gives rise to additional branches, extensions, and connections.

Angiogenic agents: Agents that act to modulate angiogenesis.

Angiogenic factors: Angiogenic polypeptides.

Anti-inflammatory agent: Agents that act to reduce in intensity or duration the physiologic process of inflammation.

Antiplatelet agents: Agents that act to inhibit or decrease platelet aggregation and/or clot formation or otherwise modulate the aggregation and/or clotting activity of platelets. Used herein as synonymous with antithrombotic agents.

Antiproliferative agents: Agents that act to modulate cell proliferation, including cell proliferation resulting from cell transformation, for example, in the cases of cancer, malignancy, neoplasms, and virus-induced cell transformations.

Antirestenotic agents: Agents that act to modulate restenosis.

Antithrombotic agents: Agents that act to modulate thrombin activity. Used herein as synonymous with antiplatelet agents.

Arteriosclerosis: Hardening of the arteries produced by degenerative or hyperplasic changes to the intima of arteries or a progressive increase in muscle and elastic tissue in arterial walls.

Atherosclerosis: The most common form of arteriosclerosis characterized by deposits of lipid material in the intima of medium and large diameter arteries, resulting in partial or total occlusion of an affected vessel.

Beneficial agent: As used herein, the term "beneficial agent" is intended to have its broadest possible interpretation and is used to include any therapeutic agent or drug, as well as inactive agents such as barrier layers, carrier layers, therapeutic layers, or protective layers.

Beneficial layers: Biodegradable layers comprising beneficial agents.

Biodegradable: See Bioresorbable, below.

Bioresorbable: The characteristic of being bioresorbable and/or able to be broken down by either chemical or physical processes, upon interaction with a physiological environment. For example, a biodegradable or bioerodible matrix is broken into components that are metabolizable or excretable, over a period of time from minutes to years, preferably less than one year, while maintaining any requisite structural integrity in that same time period.

Erosion: The process by which components of a medium or matrix are bioresorbed and/or degraded and/or broken down by chemical or physical processes. For example in reference to biodegradable polymer matrices, erosion can occur by cleavage or hydrolysis of the polymer chains, thereby increasing the solubility of the matrix and suspended beneficial agents.

Erosion rate: A measure of the amount of time it takes for the erosion process to occur, usually reported in unit-area per unit-time.

Hypoxia: Condition characterized by an abnormally low oxygen concentration in affected tissues.

Implantation site: A site into which a medical device or stent is physically implanted.

Ischemia: Local anemia resulting from obstructed blood flow to an affected tissue.

Matrix or bioresorbable matrix: The terms "matrix" or "bioresorbable matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a beneficial agent, as defined herein. A matrix is also a medium that may simply provide support, structural integrity or structural barriers. The matrix may be polymeric, non-polymeric, hydrophobic, hydrophilic, lipophilic, amphiphilic, and the like.

Openings: The term "openings" includes both through openings and recesses.

Pharmaceutically acceptable: The characteristic of being non-toxic to a host or patient and suitable for maintaining the stability of a beneficial agent and allowing the delivery of the beneficial agent to target cells or tissue.

Primarily: With respect to directional delivery, primarily refers to an amount greater than about 50% of the total amount of beneficial agent provided to a blood vessel.

Radially inner or radially interior surface: With respect to medical device struts, a radially inner or interior surface refers to a surface that has a substantially equivalent radius to that of the interior strut surface.

Radially intermediate surface: With respect to medical device struts, a radially intermediate surface refers to a surface that has a substantially equivalent radius intermediate between that of the interior and exterior strut surfaces.

Restenosis: The recurrence of stenosis after a surgical procedure, including the infiltration of smooth muscle cells into the bore of a medical device implanted to correct a previous chronic occlusion.

Sequential delivery: Delivery of beneficial agents in a specified sequence, for example where about 75% of a first agent is delivered before about 50% of a second agent is delivered.

Stenosis: A restriction or occlusion of any vessel or orifice.

Therapeutic agent: Refers to any therapeutically active substance that is delivered to a bodily conduit of a living being to produce a desired, usually beneficial, effect. The present invention is particularly well suited for the delivery of antineoplastic, angiogenic factors, immuno-suppressants, and antiproliferatives (anti-restenosis agents) such as paclitaxel and Rapamycin for example, and antithrombins such as heparin, for example.

Thrombosis: The formation of a thrombus (clot) within a blood vessel, often leading to partial or total occlusion of the blood vessel, leading to a condition of hypoxia in tissues supplied by the occluded blood vessel.

Vasodilators (or vasodilative agents): Polypeptides, polynucleotides encoding polypeptides, small molecules, or combinations thereof, that cause blood vessel dilation, i.e., an increase in the lumen of a blood vessel.

The present invention relates to the use of medical devices, and more particularly to the use of implantable medical devices having a plurality of openings in non-deforming strut and/or link elements, to deliver therapeutic agents to an implantation site over an extended period of time. In particular, the invention relates to medical devices for directional delivery of therapeutic agents and the use of medical devices to deliver different therapeutic agents, different quantities of therapeutic agents, or different release profiles of the same or different therapeutic agents in different directions with respect to the surfaces of the medical device.

The implantable bi-directional agent delivery device is useful, for example, for delivering antirestenotic, antithrombotic, antiplatelet, antiproliferative, antineoplastic, immunosuppressive, angiogenic, antiangiogenic agents, anti-inflammatories, and/or vasodilators to a blood vessel. In one embodiment of the invention, antiproliferative, antineoplastic, angiogenic, antiangiogenic, anti-inflammatory, and/or antirestenotic agents are delivered to the wall of a blood vessel and antithrombotic, antiplatelet agents, and/or vasodilators are delivered to the lumen of a blood vessel. The bi-directional delivery device can be used in many therapies particularly those where a first agent has been known to be delivered from a stent while a second agent is delivered systemically. The bi-directional delivery allows the systemically delivered agent to be delivered by the same device as the first agent.

Figure 1:
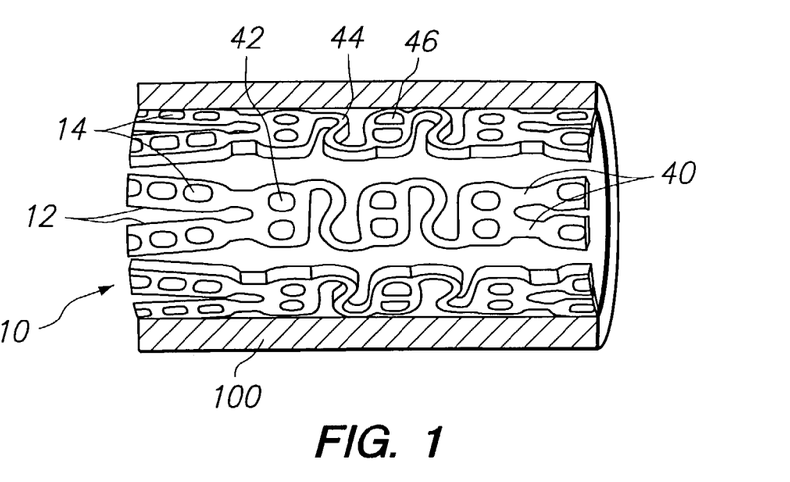
FIG. 1 is a perspective view of a portion of a medical device with beneficial agent implanted in the lumen of a blood vessel.
Figure 2:
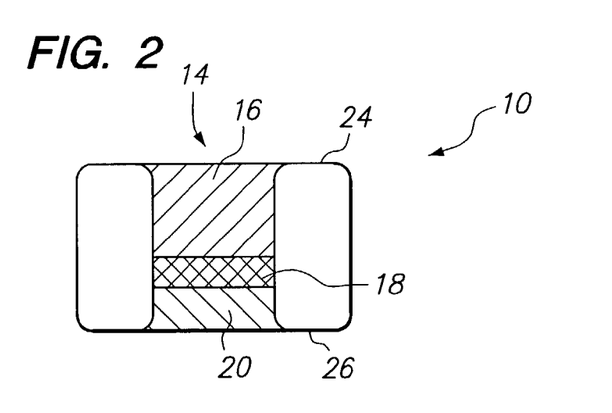
FIG. 2 is an enlarged cross-section of a portion of a medical device with openings illustrating two beneficial agents provided in one opening for bi-directional delivery.
Figure 3:
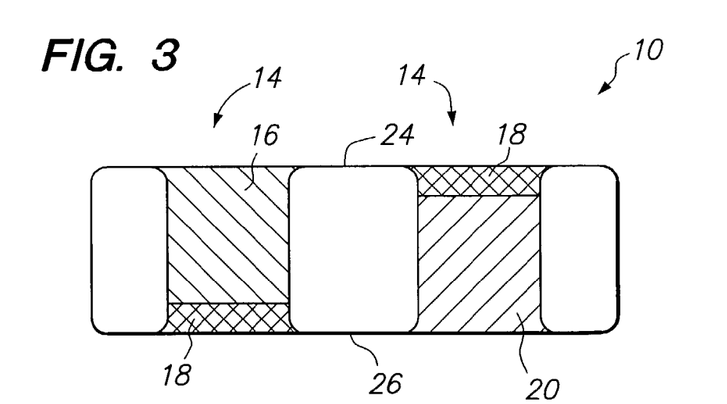
FIG. 3 is an enlarged cross-section of a portion of a medical device with openings illustrating a plurality of beneficial agents provided for bi-directional delivery from multiple openings.

FIG. 1 illustrates a portion of one example of a medical device 10 of the present invention shown disposed longitudinally in a blood vessel. FIGS. 2 and 3 show two examples of the medical device 10 of FIG. 1 in further detail. The device 10 is formed of struts and links (collectively referred to herein as struts 12) which are interconnected by ductile hinges 40. The device 10 includes openings 14 containing one or more agents. In the example of FIG. 1, a plurality of struts 12 include substantially rectangular openings 14, while other struts include substantially circular openings 42. Bridging elements 44 connect adjacent stent segments and include an arrangement of substantially D-shaped openings 46 for containing a beneficial agent. The struts 14 and portions of the bridging elements 44 having openings 14, 42, 46 are nondeforming.

In the embodiment of FIG. 1, the ductile hinges 40 allow expansion and/or compression of the medical device 10 while allowing the struts 12, and thus the openings 14 to remain undeformed during expansion or compression. The portions of the bridging elements 44 containing the openings 46 are also non-deforming. The non-deforming beneficial agent containing openings 14, 42, 46 prevent damage to or altering of the beneficial agent within the openings. The embodiment of FIG. 1 is shown as one example, however, other device structures may also be used.

FIG. 1 is a side view of a portion of the medical device 10 implanted in a lumen of a blood vessel 100. A wall of the blood vessel 100 includes three distinct tissue layers, an intima, a media, and an adventitia. The medical device 10 incorporates some of the features of the medical devices described in U.S. Pat. No. 6,241,762, herein incorporated by reference in its entirety. U.S. Pat. No. 6,241,762 describes a medical device design that remedies performance deficiencies of previous medical devices by the use of ductile hinges and non-deforming struts.

The openings 14, 42, 46 in the example of FIG. 1 extend from an exterior surface of the device adjacent the vessel wall to an interior surface or lumenal side of the device. The presence of the openings 14, 42, 46 in the medical device 10 containing beneficial agent provide a number of important advantages. For example, the openings 14, 42, 46 allow the use of a substantially larger volume of beneficial agent than can be used in the case of a coating, increasing the total amount of beneficial agent available for delivery. The ability to dispose beneficial agent in the medical device openings 14 also facilitates the gradual release of beneficial agent over an extended delivery period, compared to the use of a simple coating.

In addition, the use of openings 14, 42, 46 that contain a plurality of agents and optional barrier layers, allows the primary release of beneficial agents in one or both directions (inward and outward) relative to the implanted medical device 10 (FIG. 1). In this manner, beneficial agents may be delivered primarily to the exterior surface of the medical device 10 adjacent to the intima of the blood vessel 100, primarily to the interior surface of the medical device 10 exposed to the lumen of the blood vessel 100, or both. A barrier layer in the medical device 10 openings 14, 42, 46 is useful in minimizing diffusion of agents in the direction of the barrier layer allowing directional delivery of the agents.

FIG. 2 is a perspective view of one embodiment of a medical device 10 showing an opening 14 in the struts 12 of the device for bi-directional therapeutic agent delivery. FIG. 3 is an expanded side view of a portion of another embodiment of the medical device 10 of FIG. 1, further showing the arrangement of openings 14 in the struts 12 of the device for bi-directional agent delivery from different openings.

An enlarged cross-section view of a portion of a medical device having one or more openings 14, and one or more beneficial agents, is shown in FIG. 2. In general, the openings 14 in the struts 12 may be provided with a barrier layer 18, a first therapeutic agent 16, and a second therapeutic agent 20. In one embodiment of the invention, the total depth of an opening 14 is about 100 to about 140 microns (µM), typically about 125 microns, and the agents are delivered to the opening by depositing layers which may mix together significantly after being deposited in the opening. A typical layer thickness is about 2 to about 50 microns, preferably about 12 microns thick. There would be at least two and preferably about ten to twelve layers deposited in an opening 14, with a total beneficial agent thickness about 25 to about 28 times greater than a typical surface coating. According to one preferred embodiment of the invention, the openings 14 each have a cross-sectional area of at least about $5\times10^{-6}$ square inches, and preferably at least about $7\times10^{-6}$ square inches.

Since each layer of beneficial agent may be created independently, individual chemical agents and pharmacokinetic properties can be imparted to each layer. Numerous useful arrangements of layers can be formed, some of which will be described below. Each of the layers may include one or more therapeutic agents in the same or different proportions from layer to layer. The layers may be solid, porous, or filled with other drugs or excipients.

FIG. 3 shows a medical device 10 with a simple arrangement of layers in openings 14 with a barrier layer 18 disposed at the exterior surface 24 or interior surface 26 of the strut 12 and the first therapeutic agent 16 and second therapeutic agent 20 arranged adjacent the barrier layer for directional agent delivery. This arrangement is useful, for example, for delivering different therapeutic agents 16, 20 to the vessel wall and to the lumen of the blood vessel 100.

The therapeutic agents 16, 20 may be arranged as one or more plugs or layers. The layers may include essentially identical layers of at least one therapeutic agent, layers comprising different concentrations of at least one therapeutic agent, layers comprising different therapeutic agents, or any combination thereof, suspended in biodegradable matrices with the same or different erosion or resorbsion properties. The erosion of the biodegradable matrix results in the release of therapeutic agent at a release rate over time corresponding to the erosion rate of the matrix, providing for a controlled distribution of one or more therapeutic agents. Use of bioresorbable carriers in combination with openings is especially useful, for example, to assure essentially 100% discharge of the therapeutic agent within a predetermined period of time.

The concentration of the same therapeutic agents in the layers could be varied from layer to layer, facilitating release profiles of a predetermined shape. Progressively, increasing concentrations of therapeutic agent at layers of greater depth results in the release of the therapeutic agent at an approximately linear rate over time or a zero order delivery profile.

Alternatively, different layers may comprise different therapeutic agents, providing the ability to release different therapeutic agents at different times following implantation of the medical device 10. In one embodiment of the invention, the different layers are eroded sequentially such that the majority of the therapeutic agent 16 in a first layer at an outer surface of the device 10 is delivered before the majority of therapeutic agent of the second or underlying layer, and so forth.

In FIG. 3, when the barrier layer 18 is disposed at or near the exterior surface 24 of the medical device 10, the release of the adjacent therapeutic agent 20 is directed primarily toward the lumen of the blood vessel. In this embodiment, barrier layers 18 are disposed at or near the external surface 24 in a first subset of openings 14 and disposed at or near an internal surface 26 in a second subset of openings 14 of the medical device 10. Therapeutic agents 16 to be delivered to the wall of a blood vessel 100 upon implantation of the medical device 10 are provided in the openings having the barriers layers 18 disposed at or near the internal surface 26. Therapeutic agents 20 to be delivered to the lumen of the blood vessel upon implantation of the medical device 10 are provided in the openings having the barriers layers 18 disposed at the external surface 24. In this manner, therapeutic agents 16, 20 are delivered primarily in different directions using different subsets of openings 14, where a subset can be any number of openings less than the total number of openings. Agents are delivered primarily in a selected direction when at least 80% of the agent is delivered in the direction or preferably when at least 90% of the agent is delivered in the selected direction.

FIG. 2 illustrates another embodiment of the invention in which the barrier layer 18 is disposed at a radially intermediate position with respect to the exterior surface 24 and interior surface 26 of the medical device. The barrier layer 18 may be disposed essentially equidistant between the exterior 24 and interior 26 surfaces of the medical device 10 or may be disposed closer to either the exterior 24 or interior surface 26. Barrier layers 18 may be disposed at essentially the same radially intermediate positions in all the openings 14 of a medical device 10 or at different radially intermediate locations in different openings of the medical device 10. The presence of the barrier layer 18 creates essentially two independent reservoirs in each opening 14 for providing therapeutic agents 16, 20.

As described above, the first and second therapeutic agents 16, 20 and the barrier layer 18 may each be formed by deposition of one or more layers which may mix within the openings after deposition. The layers of therapeutic agent can include essentially identical layers of at least one therapeutic agent, layers comprising different concentrations of at least one therapeutic agent, layers comprising different therapeutic agents, or any combination thereof, suspended in biodegradable matrices with the same or different erosion properties.

Barrier layers 18 as shown in FIGS. 2 and 3, can be used to control therapeutic agent release kinetics in several ways. First, a barrier layer 18 with a substantially non-biodegradable barrier material could be used to essentially prevent the diffusion of therapeutic agents 16, 20 in one direction, thereby insuring the delivery of therapeutic agents to essentially one surface of the medical device 10. Barrier layers 18 with predetermined erosion times longer than the erosion times of the biodegradable matrix used in the therapeutic agent layers 16, 20 are also useful for directing therapeutic agents to the exterior or interior surface of the implanted medical device 10 but will eventually erode providing a termination of a treatment at a predetermined time.

The erosion rates of individual layers may be further controlled by creating contours on the surfaces of selected layers. For example, ribs on the surface of a layer increase the overall surface area and increase the rate on initial release. Elevated or protruding portions of one layer, e.g., that extend into depressed areas in another layer, cause leading or trailing characteristics of the release profiles of the therapeutic agents in the protruding or depressed layers.

In another embodiment of the invention, barrier layers 18 may be disposed in only a subset of the openings 14 in the medical device 10. The subset may comprise any number less than the total number of openings in the medical device. Openings 14 without barrier layers 18 may still be provided with therapeutic agents 16, for example, therapeutic agents intended to be delivered to both the exterior surface 24 and interior surface 26 of the medical device 10.

In another alternative, some openings may be provided with therapeutic agent 16 while others are left empty. The empty openings could provide an immediate nidus for the ingrowth of cells and extracellular components to affix the medical device 10 to the blood vessel 100, while the "filled" openings dispense therapeutic agents 16, 20.

The first and second therapeutic agents 16, 20 may be provided without a separation barrier layer when the two agents are delivered in opposite directions and are completely delivered at approximately the same time. Alternatively, where some delivery of the first and second therapeutic agents 16, 20 to the side of the medical device 10 other than the primary delivery target is acceptable or desired, the barrier layer 18 may be omitted.

A single medical device may comprise any combination of traversing openings, wherein the traversing openings may be provided with barrier layers at different positions or left empty, as described above. For example, a single medical device could comprise openings with barrier layers disposed at the interior surface of the medical device, openings with barrier layers disposed at the exterior surface of the medical device, openings with barrier layers disposed at an intermediate surface of the medical device, and empty openings.

In one embodiment of the invention, layers comprising therapeutic agents can be provided in the openings open to the exterior of the medical device, the openings open to the interior of the medical device, in openings without barrier layers, in a subset of openings, or any combinations thereof, thereby providing for the release of therapeutic agents in one or both directions as selected by the practitioner. Each layer may comprise one or more therapeutic agents and each opening may comprise one or more therapeutic layers. The release rates of therapeutic agents could be controlled independently depending on the particular bioresorbable matrix selected to deliver each therapeutic agent or each combination of therapeutic agents. Release rates and release profiles can also be controlled by adding separating layers, modification of layer thickness, selection of matrix material, and many other factors.

In one embodiment of the invention, one or more antiproliferative, antineoplastic, antiangiogenic, angiogenic, anti-inflammatory, and/or antirestenotic agents are provided in the openings open to the exterior 24 of the medical device 10 for delivery to the wall of the blood vessel 100. Also in one embodiment of the invention, one or more antithrombotic agents, antiplatelet agents, anti-inflammatory and/or vasodilators are provided in the openings open to the inside surface 26 of the medical device 10 for delivery to the lumen 116 of a blood vessel.

The therapeutic agents for use with the present invention also include classical low molecular weight therapeutic agents (commonly referred to as drugs) including but not limited to immunosuppressants, antilipid agents, anti-inflammatory agents, vitamins, antimitotics, metalloproteinase inhibitors, NO donors, estradiols, anti-sclerosing agents, and vasoactive agents, alone or in combinations with any therapeutic agent mentioned herein. Therapeutic agents also include peptides, polypeptides, polynucleotides encoding polypeptides, lipids, protein-drugs, enzymes, oligonucleotides and their derivatives, ribozymes, other genetic material, prions, viruses, bacteria, and eukaryotic cells such as endothelial cells, monocyte/macrophages or vascular smooth muscle cells to name but a few examples. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the therapeutic layer. Therapeutic agents may also be radioactive isotopes or agents activated by some other form of energy such as light or ultrasonic energy, or by other circulating molecules that can be systemically administered. Therapeutic agents may perform multiple functions including modulating angiogenesis, restenosis, cell proliferation, thrombosis, platelet aggregation, clotting and vasodilation. Anti-inflammatories include non-steroidal anti-inflammatories (NSAID), such as aryl acetic acid derivatives, e.g., Diclofenac; aryl propionic acid derivatives, e.g., Naproxen; and salicylic acid derivatives, e.g., aspirin, Diflunisal. Anti-inflammatories also include glucocoriticoids (steroids) such as dexamethasone, prednisolone, and triamcinolone. Anti-inflammatories may be used in combination with antiproliferatives to mitigate the reaction of the tissue to the antiproliferative.

The therapeutic agents delivered by the medical device of the present invention may be arranged for delivery uniformly from the entire interior and exterior surfaces of the device. Alternatively, the delivery locations of the therapeutic agents may be arranged such that two or more agents are delivered from different areas of the device. For example, a first therapeutic agent may be delivered to the wall of the blood vessel at the ends of a cylindrical medical device, a second therapeutic agent may be delivered uniformly to the lumen of the blood vessel, and a third therapeutic agent may be delivered to the vessel wall at an interior portion of the cylindrical device between the ends.

Although the present invention has been described as a generally cylindrical expandable medical device for use as a stent in a blood vessel, the device can also take on different configurations for implantations in other lumens or organs within the body where it is desirable to have directional delivery of two or more therapeutic agents.

In the illustrated embodiments, the therapeutic agents are delivered directly to the wall or lumen of the blood vessel. The therapeutic agents may also be delivered indirectly through a protective or controlling layer in the form of a layer in the openings or a coating on the device.

In one embodiment of the invention, one or more angiogenic agents are provided in openings open to the exterior surface 24 of the medical device and one or more vasodilator agents are provided in openings open to the inside surface 26 of the medical device 10. In another embodiment of the invention, one or more antiproliferative, anti-inflammatory, and/or antiangiogenic agents are provided in openings open to the exterior surface 24 of the medical device 10 and one or more vasodilator agents are provided in openings open to the inside surface 26 of the medical device.

In a further embodiment of the invention, one or more angiogenic agents are provided in openings open to the exterior surface 24 of the medical device 10 and one or more antithrombotic and/or antiplatelet agents are provided in openings open to the inside surface 26 of the medical device. In another embodiment of the invention, one or more antiproliferative, anti-inflammatory, and/or antiangiogenic agents are provided in openings open to the exterior surface 24 of the medical device 10 and one or more antithrombotic and/or antiplatelet agents are provided in openings open to the inside surface 26 of the medical device.

In yet another embodiment of the invention, one or more antirestenotic agents, including but not limited to actinomycin D, Rapamycin or paclitaxel, are provided in openings open to the exterior surface 24 of the medical device 10 and one or more vasodilators are provided in openings open to the inside surface 26 of the medical device. In another embodiment of the invention, one or more antirestenotic agents are provided in openings open to the exterior surface 24 of the medical device 10 and one or more antithrombotic and/or antiplatelet agents are provided in openings open to the inside surface 26 of the medical device.

As used herein, one or more agents include agents comprising different agents, different combinations of agents, different concentrations of the same or different agents, or combinations thereof, in one or more therapeutic layers.

In one embodiment of the invention, multiple therapeutic layers are used to provide the essentially sequential release of one or more therapeutic agents. In this manner, multiple antirestenotic, angiogenic or antiangiogenic, anti-inflammatory, and/or antiproliferative agents are delivered sequentially to the blood vessel wall while multiple, antithrombotic agents, anti-inflammatories, antiplatelet agents, and/or vasodilators are sequentially delivered to the lumen of the blood vessel. The sequence and release profiles of each therapeutic agent may be modulated by providing each therapeutic agent in specific openings, in layers with different bioerodable characteristics, in layers deposited in a specific order with respect to adjacent layers, or through any combination thereof. Accordingly, the instant invention allows the practitioner to tailor the release of therapeutic agents to particular types of treatment, to particular combinations of treatments, to the needs of particular patients, and any combinations thereof.

The presence of openings also allows layers of bioresorbable matrix to be deposited beyond the outer edge of the medical device as the matrix material disposed within the openings serves as an anchor for a cone or other protruding shape of matrix material outside the openings. The cone of matrix material could comprise, for example, the first of a number of therapeutic agents (or the first combination of therapeutic agents) to be delivered to a target capillary. Upon implantation of the medical device, the cones are forced into contact with the interior surface of the capillary, delivering the therapeutic agent in a concentrated form with minimal opportunity for diffusion of the therapeutic agents away from the target cells. In addition, cones of sufficient stiffness, as determined by the matrix material, are able to mechanically penetrate the interna or the interna and media of the target blood vessel and deliver a therapeutic agent directly to the adventitia, where therapeutic agents may be most likely to have an effect. As the outer cone of material dissolves, new layers of biodegradable matrix are exposed, delivering additional therapeutic agents to the vessel wall. In one embodiment of the invention, only the outermost layer is conical in shape. In another embodiment, more than one layer is conical in shape.

In one embodiment, the openings or wells contain one or more therapeutic polypeptides, including but not limited to angiogenic polypeptides. As used herein, polypeptides include full-length polypeptides, truncated polypeptides, chimeric polypeptides, variant polypeptides, polypeptide fragments, conjugated polypeptides, or synthetic polypeptides comprising naturally-occurring or synthetic amino acids. Any of the polypeptides may be glycosylated, phosphorylated, acylated, or otherwise modified. The invention includes the use of individual polypeptides, multiple polypeptides, polypeptides comprising multiple subunits, polypeptides requiring co-factors, and combinations thereof.

The polypeptides may be native or recombinant. The polypeptides may be obtained from natural sources or expressed in bacteria, yeast, or animal cells, including but not limited to mammalian cells. In a preferred embodiment of the invention, the polypeptides are human polypeptides. In another embodiment of the invention, the polypeptides are non-human primate polypeptides. In yet another embodiment of the invention, the polypeptides are mammalian polypeptides. In another embodiment of the invention, the polypeptides are truncated, chimeric, or variant polypeptides comprising one or more of the polypeptides referred to above.

The polypeptides may be active or inactive. Inactive polypeptides are useful, for example, for clinical experiments that require control medical devices having one or more inactive therapeutic agents. The polypeptides may further include a proteolytic cleavage site, destruction sequence, or secondary binding site for one or more modulating agents to allow modulation of polypeptide activity, specificity, or stability, coincident with or following medical device implantation.

The agents may be conjugated to other molecules to, for example, modulate their stability, hydrophilicity, hydrophobicity, activity, or ability to interact with particular receptors, cells types, or tissues. For example, polypeptides may be conjugated to heparin or heparin sulfate. In another embodiment, polypeptides are conjugated to naturally occurring or synthetic polymers. In another embodiment of the invention, polypeptides are conjugated to lipids or synthetic water soluble polymers, such as PEG or PET. The practitioner will recognize that any polypeptide conjugate known in the art to be useful for, e.g., polypeptide stability, delivery, or modulation, may be used within the scope of the invention. Any number of different conjugates may be used in the instant invention. In addition, any subset or all the polypeptides used as part of the instant invention may be fully conjugated, partially conjugated, or conjugated with different molecules and disposed in the same layer or in different layers.

Polypeptide therapeutic agents that can be used as part of the invention can be provided using polynucleotides encoding the polypeptides. Polynucleotides may be delivered using a gene therapy delivery vector, including but not limited to a retrovirus vector or an adenovirus vector. Polypeptide therapeutic agents can be combined with therapeutic polynucleotides and/or therapeutic small molecules that function through similar mechanism or different mechanisms.

According to one embodiment of the invention, angiogenic agents are delivered to a site of implantation. In a preferred embodiment of the invention, angiogenic agents are delivered to the exterior surface of the medical device. The delivery of angiogenic agents is useful, for example, for promoting the growth of blood vessels to alleviate disorders and conditions associated with chronic total occlusions, including but are not limited to distal embolization, arterial ruptures, acute myocardial infarction, myocardial infarction, groin hematomas, contrast-induced nephropathies, angina pectoris, digital microcirculation, chronic thromboembolic pulmonary hypertension, chronic subcritical ischemia, death, and other disorders of conditions resulting from chronic total coronary occlusion of coronary arteries.

The angiogenic agents may comprise one or more angiogenic polypeptides. The angiogenic polypeptides may be native or recombinant polypeptides. Examples of angiogenic polypeptides include VEGF, FGF, and HGF, matrix metalloproteinases (e.g., tPA, uPA), Ang, 1, Ang2, tissue factor, TGF-β1, PDGF-B, hepatocyte growth factor (HGF), insulin-like growth factor, epidermal growth factor, PD-ECGF, PF4, TSP-1, TNF, proliferin, plasminogen activator, IL-8, and HGF. In a preferred embodiment, the openings or wells contain VEGF polypeptides in a biodegradable matrix.

Angiogenic polypeptides may be provided using polynucleotides encoding angiogenic polypeptides. Polynucleotides may be delivered using a gene delivery vector, including but not limited to a retrovirus vector or an adenovirus vector. The angiogenic agents may also comprise angiogenic small molecules. Angiogenic agents may comprise combinations of angiogenic polypeptides, polynucleotides, and small molecules. Angiogenic agents may be delivered over a period of weeks or months following medical device implantation to stimulate local angiogenesis.

In another embodiment of the invention, vasodilators are delivered to the site of implantation. Vasodilators for use in the instant invention include but are not limited to organic nitrates (e.g., nitroglycerin, isosorbide dinitrate, isosorbide dinitrate), prostaglandins (e.g., epoprostenol, prostaglandin I2 (prostacyclin), and prostaglandin E2), phosphodiesterase inhibitors (e.g., pamrinone, mirinone, enoximone and piroximone), calcium antagonists (e.g., dihydropyridine, nifedipine amlodipine, felodipine, isradipine, nilvadipine, nisoldipine and nitrendipine), dopamine receptor agonists (e.g., fenoldopam mesylate), angiotensin-converting enzme (ACE) inhibitors (temocaprilat, enalaprilat, captopril quinapril, and perindopril), angiotensin-II receptor antagonists (losartan, RNH-6270, L158,809, PD123319), -adrenergic receptor antagonists (e.g., bunazosin), 1-adrenergic agonist e.g., carvedilol, metoprolol, and bisoprolol), and bradykinin. Kitakaze, M. et al. (2002) J. Am. Coll. Cardiol. 40:162–6; Oikawa, Y. et al. (2001) J. Am. Coll. Cardiol. 38:1188–94; Tanoue, A. et al. (2001) J. Clin. Invest. 109: 765–75; Sun, Y. P. et al. (2001) J. Cardiovasc. Pharmacol. Ther. 6:175–81; Kirsten, R. et al. (1998) Pharmacokinet. 34:457–82; Kirsten, R. (1998) Pharmacokinet. 35:9–36; Physicians' Desk Reference (2001) Medical Economics Co., Inc., Montvale, N.J.; and references within.

Additional vasodilators known in the art include but are not limited to contulakin-G (U.S. Pat. No. 6,489,298), L-arginine and type V phosphodiesterases (U.S. Pat. No. 6,476,037), include thiophene compounds (U.S. Pat. No. 6,440,948), 4,5-diaryl oxazole derivatives (U.S. Pat. No. 5,972,965), $N_6$-substituted adenosine analogues (U.S. Pat. No. 5,284,834), and nitrosothiol derivatives (U.S. Pat. No. 5,116,861), 1,4-Dihydropyridine compounds (U.S. Pat. No. 4,446,325). Any clinically acceptable vasodilator can be used to practice the instant invention, provided the vasodilator can be provided using the medical devices of the instant invention.

In another embodiment of the invention, anticoagulant agents (or anticoagulants) can be delivered to a site of implantation. Anticoagulants include compounds that inhibit vitamin K-dependent coagulation factors (e.g., coumarins), indirect inhibitors of thrombin (e.g., heparins and heparin derivatives), and direct thrombin inhibitors (DTIs) (e.g., hirudin, DuP 714, PPACK, efegatran, inogatran, melagatran, and ximelagatran). Physicians' Desk Reference (2001) Medical Economics Co., Inc., Montvale, N.J.; Van Aken, H. et al. (2001) Clin. Appl. Thromb. Hemost. 7:195–204; and references within. Any clinically acceptable anticoagulants can be used to practice the instant invention, provided the anticoagulants can be provided using the medical devices of the instant invention.

In yet another embodiment of the invention, antiplatelet agents can be delivered to a site of implantation. Antiplatelet agents include ADP receptor antagonists (e.g., ticlopidine and clopidogrel), glycoprotein (GP) IIb/IIIa receptor agonists (e.g., eptifibatide, tirofiban, and abciximab) that function through a variety of mechanisms, as well as prostaglandin inhibitors (e.g., aspirin) and phosphodiesterase inhibitors (e.g., dipyridamole and cilostazol). Physicians' Desk Reference (2001) Medical Economics Co., Inc., Montvale, N.J.; Dogne, J. M. et al. (2002) Curr. Med. Chem. 9:577–89; and references within. Any clinically acceptable antiplatelet agents can be used to practice the instant invention, provided the antiplatelet agents can be provided using the medical devices of the instant invention.

In another embodiment of the invention, immunosuppressive agents can be delivered to a site of implantation. Immunosuppressive agents include but are not limited to methotrexate and its polyglutamate derivatives, glucocorticoids, cyclophosphamide and azathiopr ine metabolites, mycophenolic acid, mizoribine, Brequinar, a leflunomide metabolite, cyclosporine, Tacrolimus, and Rapamycin. Allison, A. C. (2000) Immunopharmacology. 47:63–83; and references within.

Any of the above identified therapeutic agents may be conjugated to other molecules to, for example, increase their stability, increase their hydrophilicity, increase their hydrophobicity, modulate their activity, modulate there ability to interact with particular cell types, or to cause the therapeutic agent to be delivered simultaneously with a second therapeutic agent that causes no therapeutic effects or causes therapeutic effects through a different mechanism. For example, angiogenic polypeptides may be conjugated to heparin or heparin sulfate. In this case, heparin stabilizes the angiogenic polypeptide while also functioning as an antiplatelet agent.

While the invention has been described in detail with reference to the preferred embodiments thereof, it will be apparent to one skilled in the art that various changes and modifications can be made and equivalents employed, without departing from the present invention.

What is claimed is:

1. A drug delivery device comprising:
a medical device body having an exterior surface and an interior surface;
a plurality of openings in the device body;
a first therapeutic agent and a second therapeutic agent disposed in the openings and arranged to deliver the first therapeutic agent primarily to the exterior surface and to deliver the second therapeutic agent primarily to the interior surface; and
a bioerodible barrier layer disposed in the openings at a radially intermediate position with respect to said exterior surface and said interior surface of the medical device, and wherein said first therapeutic agent is provided at a radially exterior position with respect to the barrier layer and said second therapeutic agent is provided at a radially interior position with respect to the barrier layer.

2. The device of claim 1, wherein the openings in the medical device are through openings traversing the exterior surface and the interior surface.

3. The device of claim 1, wherein the first and second therapeutic agents are selected from the group consisting of:
a) different therapeutic agents;
b) different concentrations of therapeutic agents;
c) different release profiles of therapeutic agents;
d) anti-inflammatory; and
e) combinations of a)–d).

4. The device of claim 1, wherein the first therapeutic agent is selected from the group consisting of an angiogenic agent an anti-inflammatory agent, and an antiproliferative agent.

5. The device of claim 4, wherein the second therapeutic agent is selected from the group consisting of an antirestenotic agent, an antithrombotic agent, an antiplatelet agent, an anti-inflammatory agent, and a vasodilator.

6. The device of claim 2, wherein the through openings have a substantially uniform cross section between the interior and exterior surfaces.

7. The device of claim 1, wherein the barrier layer has a predetermined erosion time which is longer than erosion times of biodegradable matrices containing the first and second therapeutic agents.

8. The device of claim 1, wherein the first therapeutic agent is contained within a biodegradable matrix and the first therapeutic agent has a concentration variation within the matrix.

9. The device of claim 1, wherein the second therapeutic agent is contained within a biodegradable matrix and the second therapeutic agent has a concentration variation within the matrix.

10. The device of claim 1, wherein the openings are substantially non-deforming openings.

11. A drug delivery device comprising:
an exterior surface;
an interior surface;
a plurality of openings traversing said exterior surface and said interior surface, said openings having a barrier layer arranged at a radially intermediate position with respect to said exterior surface and said interior surface;
at least one first therapeutic agent in a therapeutic layer disposed at a radially exterior position with respect to said barrier layer; and
at least one second therapeutic agent in a therapeutic layer disposed at a radially interior position with respect to said barrier layer, wherein the barrier layer substantially prevents passage of the first and second therapeutic agents there through.

12. The device of claim 11, wherein the first therapeutic agent is selected from the group consisting of an angiogenic agent, an anti-inflammatory agent, and an antiproliferative agent.

13. The device of claim 12, wherein the second therapeutic agent is selected from the group consisting of an antirestenotic agent, an antithrombotic agent, an antiplatelet agent, an anti-inflammatory agent, and a vasodilator.

14. The device of claim 11, wherein the openings are substantially non-deforming openings.

15. The device of claim 11, wherein the barrier layer is bioerodible.

16. The device of claim 15, wherein the barrier has a predetermined erosion time which is longer than erosion times of biodegradable matrices containing the first and second therapeutic agents.

17. A drug delivery device comprising:
a medical device body having an exterior surface and an interior surface;
a plurality of through openings in the device body traversing the exterior surface and the interior surface;
an antirestenotic agent disposed in the openings and arranged to deliver the antirestenotic agent primarily to the exterior surface;
an ADP receptor agonist disposed in the openings and arranged to deliver the ADP receptor agonist primarily to the interior surface; and
a bioerodible barrier layer disposed at a radially intermediate position of the openings with respect to said exterior surface and said interior surface of the medical device, and wherein said first antirestenotic agent is provided at a radially exterior position with respect to the barrier layer and said ADP receptor agonist is provided at a radially interior position with respect to the barrier layer.

18. The device of claim 17, wherein the through openings have a substantially uniform cross section between the interior and exterior surfaces.

19. The device of claim 17, wherein the barrier layer has a predetermined erosion time which is longer than erosion times of biodegradable matrices containing the antirestenotic agent and the ADP receptor agonist.

20. The device of claim 17, wherein the barrier layer substantially prevents passage of the antirestenotic agent and the ADP receptor agonist there through.

* * * * *